United States Patent [19]

Getman et al.

[11] Patent Number: 4,879,398
[45] Date of Patent: Nov. 7, 1989

[54] PROCESS FOR PRODUCING 2,6-DISUBSTITUTED TYROSINE

[75] Inventors: Daniel P. Getman, St. Louis; Roy A. Periana, St. Peters; Dennis P. Riley, St. Louis, all of Mo.

[73] Assignee: Monsanto Company, St. Louis, Mo.

[21] Appl. No.: 139,999

[22] Filed: Dec. 31, 1987

[51] Int. Cl.$^4$ ............................................. C07F 7/10
[52] U.S. Cl. ..................... 556/413; 556/418; 556/419; 556/420; 556/423; 560/21; 560/22; 560/24; 560/27; 560/29; 560/30; 560/31; 560/32; 560/39; 560/40; 560/41; 562/435; 562/437; 562/443; 562/445; 562/446; 562/449
[58] Field of Search ................ 560/24, 29, 30, 31, 560/39, 41, 21, 22, 27, 32, 40; 556/413, 418, 419, 420, 423; 562/435, 437, 443, 445, 446, 449

[56] References Cited

U.S. PATENT DOCUMENTS

| | | | |
|---|---|---|---|
| 3,949,000 | 4/1976 | Violet | 260/606.5 |
| 4,119,652 | 10/1978 | Knowles et al. | 260/429 R |
| 4,261,919 | 4/1981 | Knowles et al. | 260/465 D |
| 4,331,818 | 5/1982 | Riley | 568/17 |
| 4,599,325 | 7/1986 | Hansen et al. | 514/19 |
| 4,634,775 | 1/1987 | Beck et al. | 548/402 |

FOREIGN PATENT DOCUMENTS 1501599 2/1978 United Kingdom .

OTHER PUBLICATIONS

Steric Hindrance in α-Chymotrypsin-Catalyzed Reactions; H. I. Abrash and C. Niemann; Biochemistry, 2, 947, (1963).

The Preparation of Methyl-Substituted DL-Phenylalanines, R. R. Herr, T. Enkoji and J. P. Dailey; J. American Chemical Society, 79, 4229, (1957).

Assymmetric Hydrogenations Catalysed by Diphosphinite Rhodium Complexes Derived from Natural Tartaric Acid; J. Bourson and L. Oliveros; Journal of Organometallic Chemistry, 229, 77–84, (1982).

Assymetric Hydrogenation Using Ferrocenylphosphine Rhodium (I) Cationic Complexes; W. R. Cullen and E-ShanYeh; Journal of Organometallic Chemistry, 139, C13–C16, (1977).

Structural Requirements in Chiral Diphosphine-Rhodium Complexes; Tetrahedron Letters No. 52, pp. 4639–4642, (1977), Pergamon Press, Great Britain.

Abstract; Dygas, TCM TECH Symposium at G. D. Searle & Co., (1986).

Derwent Publications Ltd., Abstracts 12030B/07; 39650 K/17; 34661C/20; O6090C/04; 87-057083/09.

*Primary Examiner*—Bruce Gray
*Attorney, Agent, or Firm*—Charles E. Smith; James W. Williams, Jr.; Arnold H. Cole

[57] ABSTRACT

A process for making 2,6-disubstituted tyrosine by the noble metal coupling of a disubstituted aromatic halide or diazonium salt with an amino-protected 2-aminoacrylic acid to form a (Z)-β-(disubstituted phenyl)-α-acylaminoacrylate, and asymmetrically hydrogenating the acrylate to produce the 2,6-disubstituted tyrosine.

12 Claims, No Drawings

PROCESS FOR PRODUCING 2,6-DISUBSTITUTED TYROSINE

FIELD OF THE INVENTION

This invention is a process for making a beta(2,6-disubstituted phenyl) amino acid. More specifically, this invention is a process for producing 2,6-disubstituted tyrosine.

SUMMARY OF RELATED ART

The preparation of a racemic mixture of 2,6-dimethyltyrosine is disclosed by H. I. Abrash and C. Niemann, Biochemistry, 2, 947 (1963). The method involves the protection of 3,5-dimethylphenol to form 3,5-dimethylphenyl ethyl carbonate which is then chloromethylated to form 3,5-dimethyl-4-chloromethylphenyl ethyl carbonate. The chloro is displaced with diethyl-2-acetamidomalonate at the 2-position to form the amido diester, which is subsequently acidolysed to form the racemic mixture of 2,6dimethyltyrosine.

The preparation of 2,6-dimethyl DL-phenylalanines is disclosed by R. R. Herr, T. Enkoji & J. P. Dailey, *J. Amer. Chem. Soc.*, 79, 4229(1957). The method involves the conversion of 2,6-dimethyl aniline into its diazonium salt, followed by treatment with potassium cyanide and cuprous cyanide to produce 2,6-dimethylbenzonitrile. The benzonitrile is reduced with lithium aluminum hydride to provide 2,6-dimethylbenzylamine, which is reacted with excess methyl iodide producing 2,6dimethylbenzyltrimethylammonium iodide. The trimethylammonium group is displaced with diethyl-2acetamidomalonate to form the amido diester, which is subsequently acidolysed to form the racemic mixture of 2,6-dimethylphenylalanine.

These methods have the disadvantage that if one enantiomer is desired, the product mixture will have to be resolved. Applicant's process has overcome this disadvantage with a process that produces predominantly the natural (levorotatory) enantiomorph.

SUMMARY OF THE INVENTION

The present invention involves a process for the production of a beta(2,6-disubstituted) phenyl amino acid of the structure:

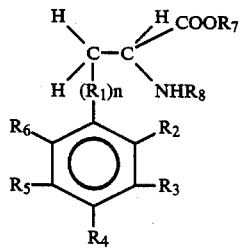

wherein
  R is methylene or ethylene,
  n is 0 or 1, $R_2$ and $R_6$ are independently alkyl, aryl, chloro, fluoro, alkoxy, carboalkoxy or nitro,
  $R_3$, $R_4$ and $R_5$ are independently hydrogen, alkyl, aryl, chloro, fluoro, alkoxy, carboalkoxy or nitro,
  $R_7$ is an acid-protecting group and
  $R_8$ is an amine-protecting group, comprising
  (1) coupling a substituted phenyl compound of the structure

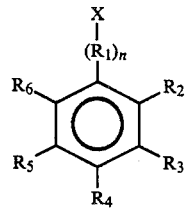

wherein X is bromo, iodo, or diazonium and n is 0 or with an acylamino acrylate of the structure

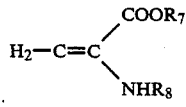

to form a substituted Z-3-(disubstituted phenyl) aminoprotected acrylate of the structure,

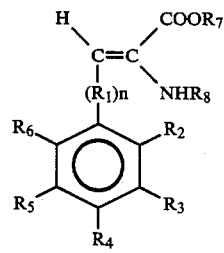

(2) asymmetrically hydrogenating the acrylate obtained to form the desired 2,6-disubstituted phenyl amino acid, and optionally, (3) deprotecting the protected 2,6-disubstituted phenyl amino acid.

M. Cutolo, et. al., Tet. Let., 24, 4603, (1983) disclose a coupling reaction involving the palladium catalyzed arylation of α-acetamidoacrylic acid. No examples of a 2,6-disubstitutedphenyl halide was disclosed.

Knowles et al, U.S. Pat. 4,261,919, Riley, U.S. Pat. 4,331,818 and Beck et al, U.S. Pat. 4,634,775 disclose the asymmetric hydrogenation of β-substituted-α-acylamidoacrylic acid. The preparation of 3-(3,4-dihydroxyphenyl)-L-alanine (L-DOPA) is disclosed in each of the above references. The above references, however, fail to disclose the hydrogenation of the 2,6-disubstituted phenylacylamino acrylate of the present invention.

None of the above references disclose the process of the present invention to produce a beta-(2,6-disubstituted phenyl) amino acid.

DETAILED DESCRIPTION OF THE INVENTION

The present invention involves a process to produce a beta-(2,6-disubstituted phenyl) amino acid by coupling a substituted phenyl compound with an acylamino acrylate to form a substituted acylamino acrylate, which is then hydrogenated to form a protected beta-(2,6-disubstituted phenyl) amino acid. Optionally, the protecting groups can be removed to form the 2,6-disubstituted phenyl amino acid.

The coupling reaction of the present invention involves the reaction of a disubstituted phenyl halide with an acylamino acrylate in the presence of a catalyst and is known in the art as the Heck reaction.

The Heck reaction is disclosed in U.S. Pat. 3,413,352, 3,574,777, 3,527,794, 3,700,727, 3,705,919, 3,763,213, 3,783,140, 3,922,299 and 3,988,358 which are hereby incorporated by reference. A catalyst suitable for the Heck reaction is a Group VIII metal, a preferred group being palladium, nickel and rhodium. A most preferred metal catalyst is palladium. Examples of suitable palladium catalysts include palladium diacetate, tetrakis(triphenylphosphine) palladium(O) and palladium dibenzylideneacetone. The preferred palladium catalyst is palladium diacetate. The catalyst concentration is not critical and can vary widely depending on reaction conditions. The concentration of the catalyst is in the range of 0.01 to 5.0 mole % based on the unsaturated organic halide. The preferred range is 1.0 to 2.0 mole % based on the unsaturated organic halide.

Optionally, a trivalent phosphorus or arsenic ligand can be used with the Group VIII metal catalyst. A trivalent phosphorus or arsenic ligand suitable for the present invention is the trialkyl, triaryl, trialkoxy, halo or triphenoxy derivative of phosphorus or arsenic or mixtures thereof. Examples of these ligands are triphenylphosphine, tri-n-butylphosphine, diphenylmethylphosphine, diphenylmethoxyphosphine, tri-methylphosphite, triethylphosphine, tri-ortho-tolylphosphine, phenyldi-n-butoxyphosphine, phosphorus trichloride, phenyldichlorophosphine, arsenic tribromide, triphenylarsine and triphenyl arsenite. The ratio of the ligand to the metal catalyst is not critical. The ratio can vary in the range of about 0.5:1 to about 10:1 mole ratio of ligand to metal catalyst.

The Heck reaction takes place in solution, in a slurry or neat. A preferred Heck reaction can be carried out using the unsaturated organic halide, a palladium catalyst, a phosphorus or arsenic ligand and a polar organic solvent that is inert to the reactants. Suitable polar organic solvents include N-methylpyrrolidone, acetonitrile, propionitrile, N-methyl formamide and dimethyl formamide (DMF). A preferred solvent is DMF.

The reaction temperature is any temperature sufficient to sustain the reaction and is in the range of about 50° C. to 175° C. A preferred reaction temperature range is from about 60° C. to about 110° C.

The Heck reaction can optionally take place in the presence of a base to absorb the acid generated in the reaction. Suitable bases are weak organic or inorganic bases that are inert to the reactants. Examples of such organic bases include trialkyl amines such as triethyl amine and tributyl amine and other inorganic bases such as sodium acetate, sodium bicarbonate and potassium bicarbonate. A preferred base is triethyl amine.

More specifically, the coupling step of the present invention is disclosed by M. Cutolo, et. al., Tet. Let., 24, 4603, (1983), which is hereby incorporated by reference. The α-acetamidocinnamic acids of the above reference are prepared by palladium catalyzed arylation of α-acetamidoacrylic acid using palladium acetate in the presence of triphenylphosphine or dichlorobis-(triphenylphosphine) palladium catalysts.

The substituted phenyl compound suitable for the coupling reaction is a substituted phenyl that minimally has a 2,6 substituent on the phenyl ring of the structure

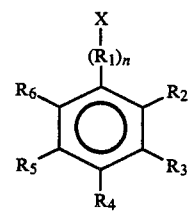

X is bromo, iodo or diazonium. Chloro and fluoro moieties typically do not couple in this reaction. A preferred X substituent is iodo, which gives unexpectedly high yields, in the range of 60 to 80 mole %. $R_1$ is a methylene or ethylene, such as methyl, or vinyl. $R_2$ and $R_3$ are independently alkyl, aryl, chloro, fluoro, alkoxy, carboalkoxy or nitro, or any substituent that will not couple with an acetamido acrylate in this reaction. Examples of suitable substituents for $R_2$ and $R_6$ are methyl, ethyl, n-propyl, iso-propyl, phenyl, benzyl, trifluoromethyl, chloro, methoxy, phenoxy, or chlorophenoxy. $R_3$, $R_4$ and $R_5$ are independently hydrogen, alkyl, aryl, chloro, alkoxy or nitro. Suitable examples are given above. Examples of suitable substituted phenyl compounds include 2,6-dimethylphenyl bromide, 2,6-dimethylphenyl iodide, 4-hydroxy-2,6-dimethylphenyl iodide, 2,6-diethylphenyl bromide, 2,4,6-triphenyl phenyl iodide, 2,6dichlorophenyl iodide, 2,4,6-trimethylphenyl iodide, 4-methoxy-2-methyl-6-trifluoromethylphenyl iodide, 4-nitro-2,6-dipropylphenyl and 2,6-dimethoxyphenyl iodide.

The acylamino acrylate suitable for the present invention is of the structure

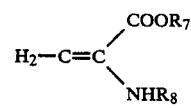

where $R_7$ is an acid protecting group and $R_8$ is an amine protecting group. Suitable amine protecting groups include acetyl, benzoyl, formyl, carbobenzoxy (CBZ), 9-fluorenylmethyloxycarbonyl (Fmoc), 2-(4-biphenyl)-propyl(2)oxycarbonyl (Bpoc), 2-phenylpropyl(2)oxycarbonyl (Poc) and t-butyloxycarbonyl (Boc). Suitable acid protecting groups include t-butyl, methyl, benzyl, beta-(trimethylsilyl)ethyl and trisubstituted silyl.

The asymmetric hydrogenation of β-substituted-α-acylamidoacrylic acid is disclosed by Knowles et al, U.S. Pat. 4,261,919, Riley, U.S. Pat. 4,331,818 and Beck et al, U.S. Pat. 4,634,775, which are hereby incorporated by reference. Any optically active coordinated metal hydrogenation catalyst known in the art to be suitable for asymmetric hydrogenation is appropriate for the process of the present invention. A suitable optically active hydrogenation catalyst used in this invention can be a coordination complex of a metal selected from the group consisting of rhodium, iridium, ruthenium, osmium, palladium and platinum, with a phosphine or arsine moiety of the formula $AR_9R_{10}R_{11}$ wherein A is phosphorus or arsenic and $R_9$, $R_{10}$, and $R_{11}$ are each independently selected from the group consisting of hydrogen, alkyl, substituted alkyl, phenyl and substituted phenyl. At least one of the moieties $AR_9R_{10}R_{11}$ must be optically active.

The hydrogenation catalyst is a complex of the formula

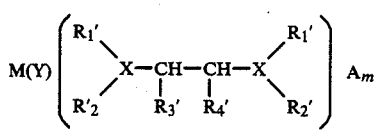

where M is a transition metal selected from a group consisting of Rh, Ir, Ru and Os, Y is a chelating diene or two monodentate olefins, $R_1$ and $R_2$ are aryl or substituted aryl groups, $R_3$ and $R_4$ are alkyl, H or aryl substitutents, X is phosphorous or arsenic, A is an anion selected from the group consisting of $PF_6^-$, $ClO_4^-$, $BF_4^-$, $CF_3SO_3^-$, $Cl^-$, and $Br^-$, and m is 1 or 2.

A preferred metal is rhodium. Examples of suitable rhodium catalyst complexes include [rhodium(1,5-cyclooctadiene)(R,R-1,2-ethanediylbis-(o-methoxyphenylphosphine] tetrafluoroborate ([Rh(COD)(R,R-DIPAMP)]BF_4), [rhodium (2,5-norbornadiene) (R-1,2-bis(diphenylphosphino)cyclohexylethane]hexafluorophosphate ([Rh(NBD)(R-Cycphos)]PF_6), [rhodium(2,5-norbornadiene)(2R,3R-bis(diphenylphosphine)-butane]perchlorate ([Rh(NBD)(R,R-Chiraphos)]ClO_4), [rhodium(1,5-cyclooctadiene)(2R, 3R-O-isopropylidene-2,3-dihydroxy-1,4-bis(diphenylphosphino)butane] tetrafluoroborate ([Rh(COD)(R, R-Diop)BF_4), [rhodium (2,5-norbornadiene)(R-1, 2-bis(diphenylphosphine)propane) perchlorate ([Rh(R-Prophos]ClO_4), [rhodium(2,5-norbornadiene) (R-1,2-bis(diphenylphosphine)phenylethane)] perchlorate ([Rh(NBD)(R-Phenphos)]ClO_4) For the preparation of [Rh(R,R-Dipamp) COD]BF_4, see Vineyard, B. D., Knolwes, W. S., Sabacky, M. J. Bachman, G. L. and Weinkauff, D. J., *J. Amer. Chem. Soc.*, 1977, 99, 5046. For the preparation of [Rh(Diop)COD]BF_4, see Kagan, H. B. and Dang, T. P., *J. Amer. Chem. Soc.*, 1972, 94, 6429. For the preparation of [Rh(R-Cycphos) NBD]PF_6, see Riley, D. P. and Shumate, R. E., *J. Org. Chem.*, 1980, 45, 5187. The catalyst concentration is not critical and can vary widely depending on reaction conditions. The catalyst concentration is in the range of 0.0001 to 5 mole %, a preferred concentration being in the range of about 1 to 2 mole %.

The reaction temperature and pressure are not critical and can be a temperature and pressure sufficient to sustain the reaction. The temperature can be in the range of about 0° C. and 100° C. A preferred range is 25° C.–70° C . The hydrogen pressure can be in the range of about 5 to 1000 psi, (34 to 6890 kPa). A preferred range is from 5 to 100 psi (34 to 689 kPa).

The asymmetric hydrogenation yields a beta-(disubstituted phenyl) amino acid of predominantly one enantiomer. The predominant enantiomorph is present in the amino acid product in 80 mole % or greater excess. Typically, the process of the present invention will yield the desired enantiomorph in 90 mole % or greater excess with excesses of 99 mole % or more observed.

The protected phenyl amino acid can be deprotected by any suitable means. Typically deprotecting is effected by strong acid treatment. Suitable acids include hydrochloric acid and hydrobromic acid.

The following examples are for illustrative purposes only and are not intended to limit the scope of the invention in any manner.

In the examples given, if the opposite enantiomorph than is shown is desired (e.g., the S rather than the R, or vice versa), it is known in the art to select the asymmetric hydrogenation catalyst complex of the opposite optical activity to produce the desired enantiomorph.

EXAMPLE 1

N-butyloxycarbonyl-2,6-dimethyl-(S)-tyrosine was prepared by the following steps:

(a) 3,5-dimethyl-4-iodophenol was prepared as follows: To a solution of 59.1 g (484 mmol) of 3,5-dimethylphenol in 1 l of methanol was added 395 ml of 36% hydrochloric acid, with occasional cooling to maintain the temperature at 20°–30° C. To the resulting solution was then added a solution of 54.3 g (327 mmol) potassium iodide and 33.5 g (157 mmol) potassium iodate in 500 ml water over a 5 minute period. The solution became red and cloudy and a tan precipitate formed. After stirring at room temperature for 20 hours, the reaction mixture was cooled in ice and the precipitate collected and washed with ice cold 2/1 (v:v) water/methanol. The resulting tan solid was recrystallized several times from hot methanol and water to yield 36.4 g (15% yield) of white needles, mp 131°–132° C., which were identified as 3,5-dimethyl-4-iodophenol. $^1H$ NMR analysis indicated the following: ($\delta$, CDCl_3) 8.03 (br s, 1H), 6.52 (s, 2H) and 2.35 (s, 6H). Mass spectrum analysis indicated the following: (m/e) 248 (m+, 100%), 121, 91 and 77.

(b) O-Methyl-3,5-dimethyl-4-iodophenol was prepared by etherifying 3,5-dimethyl-4-iodophenol as follows: In a 1 l three-necked flask equipped with an overhead stirrer were placed 63.7 g (257 mmol) of 3,5-dimethyl-4-iodophenol, 70.9 g (513 mmol) potassium carbonate, 400 ml acetone and 47.5 ml (108 g, 760 mmol) methyl iodide. The reaction mixture was refluxed for 15 hours, cooled, the precipitate filtered and washed with acetone. The combined acetone washes were concentrated under reduced pressure, dissolved in methylene chloride, washed successively with 5% sodium hydroxide, saturated sodium bisulfite and water. After drying over magnesium sulfate and filtering, the solvent was removed under reduced pressure to afford a tan oil. Recrystallization from hot methanol with cooling to room temperature and then −78° C. afforded 58.2 g (86% yield) of white needles, mp 33°–34° C., which were identified as O-methyl-3,5-dimethy-4-iodophenol. $^1H$ NMR analysis indicated: ($\delta$, CDCl_3) 6.56 (s, 2H), 3.67 (s, 3H) and 2.37 (s, 6H). Mass spectrum analysis indicated: (m/e) 262 (m+, 100%), 247, 219, 135 and 91.

(c) Methyl-(Z)-α-acetamido-β-(2,6-dimethyl-4-methoxyphenyl) acrylate was prepared by coupling O-methyl-3,5-dimethyl-4-iodophenol and methyl 2-acetamidoacrylate as follows: In a 500 ml three-necked flask equipped with an overhead stirrer (water cooled bearing), condenser and septum were placed 37.73 grams (144 mmol) O-methyl-3,5-dimethyl-4-iodophenol, 20.69 g (146 mmol) methyl 2-acetamidoacrylate, 2.17 g (7.13 mmol) tri-orthotolylphosphine and 0.61 g (2.71 mmol) palladium(II) acetate. After flushing well with argon for 15 minutes and mixing well, 43 ml (31.22 g, 309 mmol) of triethylamine, previously degassed by purging with nitrogen for 15 minutes, was added. The reaction was warmed to 100° C. over a thirty minute period in an oil bath and then held at that temperature with stirring for 14 h. After cooling to room temperature, 500 ml of methylene chloride was added and the resulting slurry was passed through 100 g of silica gel, followed by washing with 1 l of ethyl acetate. The resulting solution was then evaporated to dryness, dissolved in methylene chloride and successively washed with 10% hydrochloric acid, saturated sodium bicarbonate and saturated sodium chloride. After drying over magnesium sulfate and filtering, the solvent was removed under reduced pressure to afford 39 g of a tan solid. Recrystallization from hot ethyl acetate and hexane yielded 24.14 g (60% yield) of white needles, mp 143°–143.5° C., which were identified as Methyl-(Z)-α-acetamido-β-(2,6-dimethyl-4-methoxyphenyl) acrylate. $^1$H NMR analysis indicated: (δ, CDCl$_3$) 7.12 (br s, 1H), 6.65 (s, 2H), 6.59 (br s, 1H), 3.90 (s, 3H), 3.81 (s, 3H), 2.22 (s, 6H) and 1.99 (br s, 3H). Mass spectrum analysis indicated: (m/e) 277 (m+, 100%), 246, 235, 218, 176, 174 and 160.

(d) N-Acetyl-2,6 dimethyl-O-methyl-(S)-tyrosine methyl ester was prepared by hydrogenating methyl-(Z)-a-acetamido-β-(2,6-dimethyl-4-methoxyphenyl) acrylate as follows: In a 500 ml Fisher-Porter bottle was placed 24.18 g (87 mmol) of methyl (Z)-α-acetamido-β-(2,6-dimethyl-4-methoxyphenyl) acrylate and 1.50 g (2.0 mmol) [Rh(COD)R,R-DIPAMP)]BF$_4$. The system was taken into the dry box, sealed and removed. Through a septum was added 250 ml of methanol which had previously been purged for 1 hour with nitrogen. The system was flushed five times with 30 psig of hydrogen, charged to 30 psig hydrogen and immersed in an oil bath at 50° C. The reaction was maintained at 50° C. under 30 psig hydrogen for 16 hours. After venting and cooling, the methanol solution was concentrated at 60° C. to approximately 100 ml whereupon crystallization began to occur. After cooling to room temperature and then to 0° C., the crystals were collected and washed with cold methanol, then air dried to yield 21.42 g (88% yield) of white crystals, mp 152°–153° C., which were identified as N-Acetyl-2,6-dimethyl-O-methyl-(S)-tyrosine methyl ester. $^1$H NMR analysis indicated: (δ, CDCl$_3$) 6.59 (s, 2H), 6.14 (br d, J=8 Hz, 1H, NH), 4.78 (q, J=7.5 Hz, 1H), 3.78 (s, 3H), 3.64 (s, 3H), 3.06 (d, J=7.5 Hz, 2H), 2.33 (s, 6H) and 1.98 (s, 3H). Mass spectrum analysis indicated: (m/e) 280 (M+H), 248, 238, 220 and 149. Analysis by chiral gas chromatography using a Chirasil-Val III fused silica column showed a 99.6/0.4 mixture of S and R isomers, respectively. The mother liquors were concentrated, passed through silica gel with ethyl acetate and concentrated to yield 2.70 g of a mixture, which was shown to contain starting olefin, S-isomer and R-isomer in a 24/65/11 ratio, respectively.

(e) 2,6-Dimethyl-(S)-tyrosine hydrobromide was prepared by deprotecting N-acetyl-2,6-dimethyl-O-methyl-(S)-tyrosine methyl ester as follows: In a 100 ml round-bottom flask were placed 18.56 g (66 mmol) of N-acetyl-2,6dimethyl-O-methyl-(S)-tyrosine methyl ester, 0.63 g (3.3 mmol) sodium metabisulfite, 43 ml 48% hydrobromide acid and 21 ml acetic acid. After flushing with nitrogen, the flask was immersed in an oil bath at 120° C. and maintained there for 15 hours. After cooling, the volatiles were removed under reduced pressure at 100° C. to afford a tan solid of the desired product, contaminated with sodium metabisulfite. A sample was derivatized with Marfey's reagent and shown by HPLC analysis to be a 99.7/0.3 mixture of S and R isomers, respectively. $^1$H NMR analysis indicated: (δ, CD$_3$OD) 6.55 (s, 2H), 4.07 (br t, J=7.5 Hz, 1H), 3.32 (dd, J=7.5 and 14.1 Hz, 1H), 3.15 (dd, J=7.5 and 14.1 Hz, 1H) and 2.31 (s, 6H). Mass spectrum analysis indicated: 209 (M+), 135 (100%) and 91.

(f) The amine of 2,6-dimethyl-(S)-tyrosine hydrobromide was protected to form N-t-butyloxy-carbonyl-2,6-dimethyl-(S)-tyrosine as follows: The crude 2,6-dimethyl-(S)-tyrosine hydrobromide salt from step (e) above (approx. 66 mmol) was dissolved in 110 ml of water and 110 ml of dioxane were added. The pH was adjusted to 9 with the addition of 10% aqueous sodium hydroxide. After cooling to 20° C., 20 ml (19 g, 87 mmol) of di-t-butylpyrocarbonate was added. The reaction was maintained at a pH of between 8.5 and 8.8 by the addition of 10% sodium hydroxide and kept between 20° C. and 30° C. by occasional cooling in ice. After 1.5 hours, the pH was no longer changing and analysis by thin layer chromatography indicated the absence of free amino acid. The dioxane was removed under reduced pressure, cold 0.2N hydrochloric acid added and the resulting solids extracted into ethyl acetate. The ethyl acetate layer was separated, washed with water and saturated sodium chloride solution, dried with magnesium sulfate, filtered and removed under reduced pressure to afford a white foam, 21.21 g. This was dissolved in hot ethyl acetate and hexane added to crystallize the product. This was collected, washed with hexane and air dried to afford 16.85 g (83% yield) of a white powder, mp 165°–170° C. with decomposition, which was identified as N-t-butyloxycarbonyl-2,6-dimethyl-(S)-tyrosine. $^1$H NMR analysis indicated: (δ, d$_6$-acetone) 6.50 (s, 2H), 5.29 (br d, J=7 Hz, 1H, NH), 4.42–4.28 (m, 1H), 3.08 (dd, J=6.2 and 14.3 Hz, 1H), 2.92 (dd, J=8.5 and 14.3 Hz, 1H), 2.29 (s, 6H) and 1.37 (s, 9H). Mass spectrum analysis indicated: (m/e) 310 (M+H), 254 (100%), 210 and 164, and [α]$_D^{25}$=−13.4 (c=7.6 mg/mL, ETOH). A small sample was deprotected with 45% trifluoroacetic acid/5% anisole/50% methylene chloride, stripped, derivatized with Marfey's reagent (1-fluoro-2,4-dinitro-5-L-alanine amide) and analyzed by HPLC, which showed a 99.7/0.3 mixture of S and R isomers, respectively.

EXAMPLE 2

N-Butyloxycarbonyl-2,6-dimethyl-(5)-tyrosine was prepared by the following steps:

(a) 0-Benzyl-3,5-dimethyl-4-iodophenol was prepared as follows: In a 500 ml round-bottom flask were placed 30.0 g (121 mmol) of 3,5-dimethyl-4-iodophenol, 190 ml acetone, 16.9 g (122 mmol) potassium carbonate and 20.7 g (121 mmol) benzyl bromide. The mixture was refluxed for 15 hours, cooled, filtered and the precipitate washed with acetone. The combined filtrate was evaporated under reduced pressure to yield an orange oil which slowly crystallized. This was dissolved in methylene chloride and water and the methylene chloride layer sequentially washed with 5% sodium hydroxide, saturated sodium bisulfite and water. After drying over magnesium sulfate and filtering, the methylene chloride was removed under reduced pressure. The resulting solid was recrystallized from hot methanol, cooled to room temperature and then in ice, collected and washed with cold methanol to yield 27.9 g (68% yield) of white plates, mp 56–57, which were identified as O-Benzyl3,5-dimethyl-4-iodophenol. $^1$H NMR analysis indicated: (δ, CDCl$_3$) 7.68 (m, 5H), 6.62 (s, 2H), 4.88 (s, 2H) and 2.39 (s, 6H). Mass spectrum analysis indicated: (m/e) 338 (M+) and 91.

(b) Methyl (Z)-α-acetamide-β-(2,6-dimethyl-4-benzyloxyphenyl)acrylate was prepared by coupling 0-benzyl-3,5-dimethyl-4-iodophenol with methyl 2-acetamide-acrylate as follows: In a 100 ml round-bottom flask was placed 9.99 g (29.5 mmol) O-benzyl- 3,5dimethyl-4-iodophenol, 4.46 g (31.4 mmol) methyl 2-acetamidoacrylate, 0.49 g (1.6 mmol) tri-ortho-tolyphosphine and 141 mg (0.63 mmol) palladium(II) acetate. The flask was evacuated and argon added. This was repeated five times. To the reaction was then added 8.5 ml (6.2 g, 61 mmol) of triethylamine (previously degassed by purging with nitrogen for 15 minutes). The mixture was then warmed to 100° C. over 15 minutes and maintained there for 15 hours. After cooling to room temperature, ethyl acetate was added and the slurry filtered through silica gel, which was then eluted with ethyl acetate. The combined ethyl acetate washes were extracted with 10% hydrochloric acid and saturated sodium chloride, dried over magnesium sulfate, filtered and concentrated under reduced pressure to afford a tan solid. This was recrystallized from hot ethyl acetate and hexane to yield 7.28 g (70% yield) of whit needles, mp 138–139, which were identified as methyl (Z)-α-acetamido-β-(2,6-dimethyl-4-benzloxyphenyl) acrylate. $^1$H NMR analysis indicated: ($\delta$, CDCl$_3$) 7.18 (m, 5H), 6.99 (s, 1H), 6.63 (br s, 1H), 6.58 (s, 2H), 4.90 (s, 2H), 3.74 (s, 3H), 2.12 (s, 6H) and 1.86 (s, 3H). Mass spectrum analysis indicated: (m/e) 353 (M+), 262, 220 and 91 (100%).

(c) N-Acetyl-2,6-dimethyl-(S)-tyrosine methyl ester was prepared by hydrogenating methyl-(Z)-α-acetamide β-(2,6-dimethyl-4benzyloxyphenyl) acrylate as follows: In a 500 ml Fisher Porter bottle were placed 6.55 g (18.5 mmol) of methyl (Z)α-acetamido-β-(2,6-dimethyl-4-benzyloxyphenyl) acrylate and 141 mg (0.19 mmol) of [Rh(COD)R,R-DIPAMP)]BF$_4$.

The bottle was taken into the dry box and sealed. After removal from the dry box, 90 ml of methanol (previously purged with nitrogen for one hour) was added. The system was flushed five times with 40 psig nitrogen, then three times with 30 psig hydrogen and then pressurized to 30 psig hydrogen. The reactor was then warmed to 50° C. and maintained under 30 psig hydrogen for twenty-four hours. After cooling to room temperature and venting, the reaction solution was filtered and the filtrate was concentrated under reduced pressure. The resulting material was chromatographed on a Waters Prep 500 Chromatagram using 50% ethyl acetate/hexane (v:v) to afford 6.5 g of a white solid; $^1$H NMR spectrum indicated approximately 20% debenzylation. This material was then dissolved in 90 ml of degassed methanol, 2.0 g of 5% palladium on carbon added under nitrogen and then hydrogenated under 30 psig (207 kPa) hydrogen at room temperature for twenty hours. After venting and flushing with nitrogen, the reaction was filtered and the filtrate concentrated under reduced pressure to afford 4.24 g of a white solid. This was crystallized from hot chloroform and hexane to yield 3.40 g (69%) of white crystals, mp 156–157° C., identified as N-acetyl-2,6-dimethyl-(S)-tyrosine methyl ester. $^1$H NMR analysis indicated: ($\delta$, CDCl$_3$) 8.55 (br s, 1H), 7.80 br d, J=7 Hz, 1H, NH), 6.38 (s, 2H), 4.52 (q, J=7 Hz, 1H), 3.53 (s, 3H), 3.10–2.80 (m, 2H), 223 (s, 6H) and 1.92 (s, 3H). Mass spectrum analysis indicated: (m/e) 265 (M+), 206 and 135 (100%).

(d) 2,6-Dimethyl-(S)-Tyrosine hydrochloride was prepared by deprotecting N-acetyl-2,6-dimethy-(S)-tyrosine methyl ester as follows: In a 100 ml round-bottom flask was placed 3.40 g (13 mmol) of N-acetyl-2,6-dimethyl-(S)-tyrosine methyl ester and 20 mL of 6N hydrochloric acid. The reaction mixture was refluxed under argon for 4½ hours, cooled and then concentrated under reduced pressure to afford 3.48 g of a white solid; $^1$H NMR analysis indicated: ($\delta$, CD$_3$OD) 6.35 (s, 2H), 3.90 (t, J=7 Hz, 1H), 3.3–3.0 (m, 2H) and 2.21 (s, 6H). Mass spectrum analysis indicated: (m/e) 209 (M+), 135 (100%) and 91.

(e) The amine of 2,6-dimethyl-(S)-tyrosine hydrochloride was deprotected to form N-t-Butyloxy-carbonyl-2,6-dimethyl-(S)-tyrosine as follows: The crude 2,6-dimethyl-(S)-tyrosine hydrochloride from the step above (approx. 13 mmol) was dissolved in 20 ml of water and then 20 ml of dioxane was added. The pH of the solution was adjusted to 8.5 by the addition of 5% aqueous sodium hydroxide solution. The temperature of the reaction was maintained between 20° and 30° C. by occasional cooling in ice, and 3.1 ml (2.95 g, 13.5 mmol) of di-t-butylpyrocarbonate was added all at once. The pH was maintained between 8.5 and 8.8 by the addition of 5% sodium hydroxide solution. After approximately two hours, the pH of the solution had stopped changing and analysis by thin layer chromatography indicated the absence of free amino acid. The dioxane was removed under reduced pressure, cold 0.2N hydrochloric acid added and the resulting solids extracted into ethyl acetate. The ethyl acetate layer was separated, washed with water and saturated sodium chloride solution, dried with magnesium sulfate, filtered and removed under reduced pressure to afford 4.08 g of a white solid. This was dissolved in hot ethyl acetate and hexane added to crystallize the product, which was collected, washed with hexane and air dried to yield 3.34 g (83% yield) of a white solid, mp 173°–176° with decomposition. This was identified as N-t-butyloxycarbonyl-2,6-dimethyl-(S)-tyrosine. $^1$H NMR and mass spectrum were identical to the previously prepared material. An HPLC analysis of this material after deprotecting and derivatization with Marfey's reagent showed a 98:2 mixture of S and R enantiomers, respectively.

EXAMPLE 3

The asymmetric hydrogenation of methyl (Z)-α-acetamido-β-(2,6-dimethyl-4-methoxyphenyl)acrylate was effected with the following various chiral rhodium catalysts. Methyl (Z)-α-acetamido-β-(2,6-dimethyl-4-methoxyphenyl)acrylate was hydrogenated to N-acetyl-2,6-dimethyl-O-methyl-(S)-tyrosine methyl ester following the procedure shown above, but using several chiral rhodium catalyst. The S:R enantiomer ratios using the different catalysts were as follows; [Rh(COD)(R,R-DIPAMP)]BF$_4$ (96:4), [Rh(COD)(R,R-Diop)]BF$_4$ (83:17) and [Rh(NBD)(R-Cycphos)]PF$_6$ (93:7).

EXAMPLE 4

N-t-Butyloxycarbonyl-6-methyl-2-(a,a,a-trifluoromethyl)-(S)-tyrosine was prepared in the following steps:

(a) 4-Methoxy-2-($\alpha,\alpha,\alpha$-trifluoromethyl)nitrobenzene was prepared as follows: In a 2 l three-necked flask equipped with an overhead stirrer and condenser, was placed 75.4 g (0.334 moles) of 5-chloro-2-nitrobenzotrifluoride. After placing the reaction flask under a nitrogen atmosphere, 1 l (0.50 mole) of a 0.5M solution of sodium methoxide in methanol was added all at once. This was then refluxed for sixteen hours, cooled and the volatiles removed under reduced pressure. Cold water was added, followed by methylene chloride. The layers were separated and the organic layer successively washed with water and saturated sodium chloride solution. After drying over magnesium sulfate and filtering, the solvent was removed under reduced pressure to afford 68.7 g of a yellow solid. This was recrystallized from methanol and water to yield 54.9 g (75% yield) of light yellow crystals, which were identified as 4-methoxy-2-($\alpha,\alpha,\alpha$-trifluoromethyl)nitrobenzene; $^1$H NMR analysis indicated: ($\delta$, CDCl$_3$) 7.91 (d, J=9 Hz, 1H), 7.18 (dd, J=2 and 9 Hz, 1H), 7.02 (d, J=2 Hz, 1H) and 3.92 (s, 3H).

(b) 4-Methoxy-2-($\alpha,\alpha,\alpha$-trifluoromethyl)aniline prepared by aminating 4-methoxy-2-($\alpha,\alpha,\alpha$-trifluoromethyl)nitrobenzene as follows: In a 300 ml stainless steel autoclave was placed a solution of 25.0 g (0.11 mole) of 4-methoxy-2-($\alpha,\alpha,\alpha$-trifluoromethyl)nitrobenzene in 150 ml of 95% ethanol. After flushing with nitrogen, 1.1 g of 5% palladium on carbon was added and the autoclave sealed. After flushing with nitrogen, the reactor was charged with 60 psi (413 kPa) of hydrogen and stirred. Gas uptake began immediately and the temperature was maintained between 25° C. and 30° C. by occasional cooling with an ice bath. After approximately ninety minutes, the gas uptake had ceased. The autoclave was vented, flushed with nitrogen and opened. The catalyst was filtered off and the filtrate was concentrated under reduced pressure to afford 22 g (100% yield) of a light yellow oil which was shown to be 4-methoxy-2-($\alpha,\alpha,\alpha$-trifluoromethyl)aniline. $^1$H NMR analysis indicated: ($\delta$, CDClz) 7.82 (dd, J=2 and 9 Hz, 1H), 7.00 (d, J=2 Hz, 1H), 6.48 (d, J=9 Hz, 1H), 3.87 (br s, 2H) and 3.60 (s, 3H). Mass spectrum analysis indicated: (m/e) 191 (M+), 176, 156, 128 and 52. It was used directly in the next step without purification.

(c) 4-Methoxy-6-(methylthiomethyl)-2-($\alpha,\alpha,\alpha$-trifluoromethyl)aniline was prepared by substituting 4-methoxy-2-($\alpha,\alpha,\alpha$-trifluoromethyl)aniline as follows: In a 250 ml three-necked flask equipped with an overhead stirrer was placed 20.12 g (0.105 mol) of 4-methoxy-2-($\alpha,\alpha,\alpha$-trifluoromethyl)aniline in 100 ml of methylene chloride. To the solution was then added 15.63 g (0.117 mol) of N-chlorosuccinimide was added with vigorous stirring. After cooling to 0° C. under a nitrogen atmosphere, a solution of 9.2 ml (8.02 g, 0.129 mol) dimethylsulfide in 40 ml of methylene chloride was then added over a one hour period while maintaining the temperature below 5° C. The reaction mixture became very thick. The ice bath was removed and after stirring at room temperature for one hour, 200 ml of ice cold 5% aqueous sodium hydroxide solution was added. The methylene chloride layer was separated, dried over anhydrous potassium carbonate, filtered and the solvent removed under reduced pressure. To the residue was then added 60 ml of 1,2-dichloroethane and 1.00 g (10 mmol) of succinimide. After refluxing for twelve hours under a nitrogen atmosphere, the reaction mixture was cooled, washed twice with 100 ml of 5% sodium hydroxide solution, dried with magnesium sulfate, filtered and concentrated under reduced pressure to afford 24.9 g of a black oil. This was distilled under reduced pressure to afford 16.5 g (63% yield) of the desired product as a clear, colorless liquid (Bp 106°-110° at 0.35 mm Hg) of 95% purity as assayed by gas chromatography; $^1$H NMR analysis indicated: ($\delta$, CDCl$_3$) 6.94 (d, J=1.8 Hz, 1H), 6.78 (d, J=1.8 Hz, 1H), 4.32 (br s, 2H, NHz), 3.54 (s, 3H), 3.51 (s, 2H) and 1.82 (s, 3H). Mass spectrum analysis indicated: (m/e) 251 (M+), 204 (100%) and 181.

(d) 4-Methoxy-6-methyl-2-($\alpha,\alpha,\alpha$-trifluoro-methyl)aniline was prepared by deprotecting 4-methoxy-6-(methylthiomethyl)-2-($\alpha,\alpha,\alpha$-trifluoromethyl)aniline as follows: In a 300 ml Hastelloy C autoclave were placed 16.4 g (0.065 mol) of 4-methoxy-6-(methylthiomethyl)2-$\alpha,\alpha,\alpha$-trifluoromethyl)aniline, 8.0 g of a Co:Mo(S) catalyst (Co:Mo=1:1) (see S. J. Tremont and P. L. Mills, J. of Catalyl., 1986, 97, 252) and 100 ml of toluene. The system was flushed three times with 500 psi (3445 kPa) of nitrogen and then three times with 500 psi (3445 kPa) of hydrogen. The autoclave was charged with 1000 psi (6890 kPa) of hydrogen, heated to 200° C. and then the hydrogen pressure increased to 2000 psi (13780 kPa). After four days at 200° C. and 2000 psi hydrogen, the autoclave was cooled, vented, flushed with nitrogen and emptied. The catalyst was removed by filtering and the toluene removed under reduced pressure at 50° C. to yield 12.5 g of an oil, which was distilled to afford 9.4 g (70% yield) of a clear colorless oil (Bp 50–54 at 0.15 mm Hg) which was identified as 4-methoxy-6-methyl-2-($\alpha,\alpha,\alpha$-trifluoromethyl)aniline $^1$H NMR analysis indicated: ($\delta$, CDCl$_3$) 6.71 (m, 2H), 3.72 (br s, 2H, NH), 3.56 (s, 3H) and 2.06 (s, 3H). Mass spectrum analysis indicated: (m/e) 205 (M ), 190, 170 and 142.

(e) 4-Methoxy-6-methyl-2-($\alpha,\alpha,\alpha$-trifluoromethyl)iodo-benzene was prepared by coupling 4-methoxy-6-methyl-2-($\alpha,\alpha,\alpha$-trifluoromethyl)aniline as follows: In a 250 ml three-necked flask equipped with an overhead stirrer was placed 25 ml of concentrated hydrochloric acid. After cooling to −20° C., 9.3 g (45 mmol) of 4-methoxy-6-methyl-2-($\alpha,\alpha,\alpha$-trifluoromethyl)aniline was added over a five minute period. A thick white precipitate of the hydrochloride salt was formed. To the resulting slurry was slowly added over fifteen minutes a solution of 3.81 g (55 mmol) of sodium nitrite in 15 ml of water. The cooling bath was replaced with an ice bath and after stirring for ten minutes, a solution of 40 g (240 mmol) of potassium iodide in 100 ml of water was added over fifteen minutes. The ice bath was removed and the reaction stirred at room temperature for fifteen hours. Methylene chloride was added, the layers separated and then the organic layer washed with 10% sodium hydroxide, saturated sodium bisulfite and water, dried with magnesium sulfate, filtered and concentrated under reduced pressure to afford 13.4 g of a brown oil which solidified. This was dissolved in 150 ml of methanol, filtered, water added to the cloud point and slowly allowed to crystallize. In this manner, 10.0 g (70% yield) of slightly tan crystals were obtained, mp 38°-39° C., and identified as 4-methoxy-6-methyl-2-($\alpha,\alpha,\alpha$-trifluoromethyl)iodobenzene; $^1$H NMR analysis indicated: ($\delta$, CDCl$_3$) 6.93 (d, J=1.8 Hz, 1H), 6.85 (d, J=1.8 Hz, 1H), 3.71 (s, 3H) and 2.46 (s, 3H). Mass spectrum analysis indicated: (m/e) 316 (M+).

(f) Methyl (Z)-$\alpha$-acetamido-$\beta$-[4-methoxy-6-methyl-2($\alpha,\alpha,\alpha$-trifluoromethyl)phenyl]acrylate was prepared by coupling 4-methoxy-6-methyl-2-($\alpha,\alpha,\alpha$-trifluoromethyl) 2-acetamido-acrylate as follows: In a 100 ml round-bottom flask equipped with a stir bar were placed 9.72 g (30.7 mmol) of 4-methoxy-6-methyl-2-($\alpha,\alpha,\alpha$-trifluoromethyl)iodobenzene, 4.80 g (33.8 mmol) of methyl 2-acetamidoacrylate, 468 mg (1.54 mmol) tri-ortho-tolyphosphine and 138 mg (0.62 mmol) of palladium (II) acetate. After swirling to mix well, the flask was evacuated and then argon added. This was repeated five times. Under an argon flow, 9 ml (6.5 g, 65 mmol) of triethylamine (previously purged with nitrogen for ten minutes) was added, the reaction warmed to 100° C. over thirty minutes and then maintained there for twenty hours. After cooling to room temperature, methylene chloride was added and the slurry passed thru silica gel, which was then washed with ethyl acetate. The combined filtrates were concentrated under reduced pressure, redissolved in methylene chloride and washed with 10% hydrochloric acid, dried over magnesium sulfate, filtered and concentrated under reduced pressure to afford 9.44 g of residue, which was shown by gas chromatography to be a 40:60 mixture of starting iodide and the desired product, respectively. This was chromatographed using a Waters Prep 500A Chromatogram using silica gel and eluting with 25% ethyl acetate/hexane (v:v) to yield 2.90 g of product. This was recrystallized from hot ethyl acetate and hexane to give 2.09 g (21% yield) of white needles which were identified as methyl (Z)-α-acetamido-β-[4-methoxy-6-methyl-2-($\alpha,\alpha,\alpha$-trifluoromethyl) phenylacrylate, mp 154°–155° C.; $^1$H NMR analysis indicated: ($\delta$, CDCl$_3$) 6.95 (br s, 1H), 6.78 (d, J=1.8 Hz, 1H), 6.64 (d, J=1.8 Hz, 1H), 6.37 (br s, 1H), 3.63 (s, 3H), 3.60 (s, 3H), 2.02 (s, 3H) and 1.72 (s, 3H). Mass spectrum analysis indicated:(m/e) 331 (M ), 289, 230 (100%) and 43.

(g) N-Acetyl-6-methyl-2-($\alpha,\alpha,\alpha$-trifluoromethyl)-O-methyl-(S)-tyrosine methyl ester was prepared by hydrogenating (Z)-α-acetimido-β-[4-methoxy-6-methyl-2-($\alpha,\alpha,\alpha$-trifluoromethyl)-phenyl]acrylate as follows: In a 250 ml Fisher-Porter bottle were placed 2.00 g (6.0 mmol) of methyl (Z)α-acetamido-β-[4-methoxy-6-methyl-2-($\alpha,\alpha,\alpha$-trifluoromethyl)phenyl]acrylate and 238 mg (0.31 mmol) of [Rh(COD)(R,R-DIPAMP)]BF$_4$. The bottle was taken into the dry box and sealed. After removal from the dry box, 20 ml of methanol (previously purged with nitrogen for one hour) was added. The system was flushed five times with 40 psig (276 kPa) of nitrogen, then three times with 30 psig (207 kPa) of hydrogen and then pressurized with 30 psig (207 kPa) of hydrogen. The reactor was then warmed to 50° C. and maintained under 30 psig of hydrogen for twenty-four hours. After cooling to room temperature and venting, the solution was concentrated under reduced pressure to afford a residue. This was chromatographed on a 4 mm silica gel plate using a chromatatron to afford 1.93 g (96% yield) of a white solid which was identified as N-acetyl-6-methyl-2-($\alpha,\alpha,\alpha$-trifluoromethyl)-O-methyl-(S)-tyrosine methyl ester, mp 158°–158.5° C.; $^1$H NMR analysis indicated: ($\delta$, CDCL$_3$/d$_6$-DMSO) 6.81 (d, J=8 Hz, 1H, NH), 6.69 (d, J=1.8 Hz, 1H), 6.62 (d, J=1.8 Hz, 1H), 4.54 (q, J=7 Hz, 1H), 3.50 (s, 3H), 3.31 (s, 3H), 2.86 (AB of ABX, 2H), 2.18 (s, 3H) and 1.64 (s, 3H). Mass spectrum analysis indicated: (m/e) 333 (M ), 274 and 203 (100%). Analysis of this material by chiral gas chromatography showed a 97.6/2.4 mixture of S and R isomers, respectively.

(h) 6-Methyl-2-($\alpha,\alpha,\alpha$-trifluoromethyl)-(S)-tyrosine hydrobromide was prepared by deprotecting N-acetyl-6-methyl-2-($\alpha,\alpha,\alpha$-trifluoromethyl)-O-methyl-(S)-tyrosine methyl ester as follows: In a 25 ml round-bottom flask were placed 1.83 g (5.5 mmol) of N-acetyl-6-methyl-2-($\alpha,\alpha,\alpha$-trifluoromethyl)-O-methyl-(S)-tyrosine methyl ester, 51 mg (0.27 mmol) of sodium metabisulfite, 4 ml of 48% hydrobromic acid and 2 ml of acetic acid. After flushing with nitrogen, the mixture was placed i an oil bath at 120° C. for twenty hours, cooled and concentrated under reduced pressure to afford a brown solid which was shown to be 6-methyl-2-($\alpha,\alpha,\alpha$-trifluoromethyl)-(S)-tyrosine hydrobromide, contaminated with sodium metabisulfite. $^1$H NMR analysis indicated: ($\delta$, CD$_3$OD) 6.85 (m, 2H), 4.06 (t, J=7 Hz, 1H), 3.28 (d, J=7 Hz, 2H) and 2.36 (s, 3H). Mass spectrum analysis indicated: (m/e) 264 (M+1), 189, 81 and 74. A sample was derivatized with Marfey's reagent and analyzed by high pressure liquid chromatography and shown to be a 96.4/3.6 ratio of S and R isomers, respectively.

(i) The amine of 6-methyl-2-($\alpha,\alpha,\alpha$-trifluoromethyl)-(S)-tyrosine hydrobromide was protected to form N-t-butyloxycarbonyl-6-methyl-2-($\alpha,\alpha,\alpha$-trifluoromethyl)-(S)-tyrosine as follows: The crude 6-methyl-2-($\alpha,\alpha,\alpha$-trifluoromethyl)-(S)tyrosine hydrobromide salt from above (approx. 5.5 mmol) was dissolved in 8 ml of water and 8 ml of dioxane was added. After bringing the pH to 8.8 by the addition of 5% sodium hydroxide solution, the mixture was cooled to 15° C., 1.4 ml (1.45 g) of di-t-butylpyrocarbonate was added and the ice bath removed. The pH was maintained between 8.5 and 8.8 by the addition of 5% sodium hydroxide solution. After two hours, the pH had stabilized and analysis by thin layer chromatography indicated the absence of the free amino acids. The dioxane was removed under reduced pressure, ice cold 0.2N hydrochloric acid added and the precipitate extracted into ethyl acetate. After washing with water and saturated sodium chloride solution, drying with magnesium sulfate and filtering, the solvent was removed under reduced pressure to afford 1.73 g of a white foam. This was recrystallized from methylene chloride/hexane to yield 1.05 g (53% yield) of white needles, which were identified as N-t-butyloxycarbonyl-6-methyl-2-($\alpha,\alpha,\alpha$-trifluoromethyl)-(S)-tyrosine, mp 150°–152° C.; $^1$H NMR analysis indicated: ($\delta$, d$_6$ acetone) 7.00 (s, 1H), 6.93 (s, 1H), 5.95 (d, J=7.3 Hz, 1H, NH), 4.60–4.50 (m, 1H), 3.33 (dd, J=7 and 14 Hz, 1H), 3.23 (dd, 10 and 14 Hz, 1H), 2.43 (s, 3H) and 1.35 (s, 9H). Mass spectrum analysis indicated: (m/e) 386 (M+Na), 364 (M+H), 308, 264 and 189. Elemental analysis was performed and calculated as follows: calcd. C$_{16}$H$_{20}$F$_3$NO$_5$, C(52.89), H(5.55) and N(3.76), found C(52.78), H(5.54) and N(3.76). A small sample was deprotected, derivatized with Marfey's reagent and analyzed by HPLC and shown to be a 96/4 mixture of S and R isomers, respectively.

EXAMPLE 5

N-Butyloxycarbonyl-2,6-diethyl-(S)-tyrosine was prepared as follows: The procedures used were the same as those used to prepare N-butyloxycarbonyl-2,6-dimethyl-(S)-tyrosine in Example 1. The physical characterization of the various intermediates is listed below.

(a) 3,5-Diethyl-4-iodophenol; $^1$H NMR analysis indicated: ($\delta$, CDCl$_3$) 6.52 (s, 2H), 5.47 (br s, 1H, OH), 2.71 (q. J=7 Hz, 4H) and 1.17 (t, J=7 Hz, 6H). Mass spectrum analysis indicated: (m/e) 276 (M ) and 261.

(b) O-Methyl-3,5-diethyl-4-iodophenol; $^1$H NMR analysis indicated: ($\delta$, CDCl$_3$) 6.32 (s, 2H), 3.45 (s, 3H), 2.52 (q, J=7 Hz, 4H) and 0.98 (t, J=7 Hz, 6H), Mass spectrum analysis indicated: (m/e) 290 (M+), 275 and 105.

(c) Methyl (Z)-α-acetamido-β-(2,6-diethyl-4methoxyphenyl)acrylate; $^1$H NMR analysis indicated: ($\delta$, CDCl$_3$) 7.02 (s, 1H), 6.62 (s, 2H), 6.57 (br s, !H, NH), 3.78 (s, 3H), 3.74 (s, 3H), 2.50 (q, J=7 Hz, 4H), 1.91 (s, 3H) and 1.16 (t, J=7 Hz, 6H). Mass spectrum analysis indicated: (m/e) 305 (M+), 246 and 187.

(d) N-Acetyl-0-methyl-2,6-diethyl-(S)-tyrosine methyl ester; This was obtained as a 97/3 mixture of S and R isomers, respectively, from the asymmetric hydrogenation step using the [Rh(COD)(R,R-DIPAMP)]BF$_4$ catalyst; H NMR analysis indicated: (δ, CDCl$_3$) 6.36 (s, 2H), 6.12 (br d, J=7 Hz, 1H, NH), 4.60 (q, J=7 Hz, 1H), 3.65 (s, 3H), 3.49 (s, 3H), 2.96 (AB of an ABX, 2H), 2.59 (q, J=7 Hz, 4H), 1.89 (s, 3H) and 1.26 (t, J=7 Hz, 6H). Mass spectrum analysis indicated: (m/e) 307 (M+), 248, 177 and 43.

(e) 2,6-Diethyl-(S)-tyrosine hydrobromide salt; $^1$H NMR analysis indicated: (δ, CD$_3$OD) 6.48 (s, 2H), 3.91 (t, J=7 Hz, 1H), 3.22 (AB of an ABX, 2H), 2.57 (q, J=7 Hz, 4H) and 1.22 (t, J=7 Hz, 6H). Mass spectrum analysis indicated: (m/e) 238 (M+1), 163, 82 and 80.

(f) N-t-Butyloxycarbonyl-2,6-diethyl-(S)tyrosine; mp 145-145.5, $^1$H NMR analysis indicated: (δ, d$_6$-acetone) 6.57 (s, 2H), 6.09 (d, J=7 Hz, 1H, NH), 4.38-4.27 (m, 1H), 3.08 (dd, J=6.4 and 14.5 Hz, 1H), 3.02 (dd, J=9.2 and 14.5 Hz, 1H), 2.69 (q, J=7.0 Hz, 4H), 1.38 (s, 9H) and 1.18 (t, J=7.0 Hz, 6H). Mass spectrum analysis indicated: (m/e) 360 (M+Na), 338 (M+H), 282, 238 and 163. Elemental Analysis was performed and calculated as follows: C$_{18}$H$_{27}$NO$_5$: C(64.06), H(8.06) and N(4.15), found: C(64.17), H(8.10) and N(4.11). The final material was shown to be a 97/3 mixture of S and R isomers, respectively.

EXAMPLE 6

N-Butyloxycarbonyl-2-ethyl-6-methyl-(S)tyrosine was prepared by the procedure used to prepare N-butyloxycarbonyl-2,6-dimethyl-(S)-tyrosine in Example 1. The physical characterization of the various intermediates is listed below.

(a) 3-Ethyl-4-iodo-5-methylphenol; $^1$H NMR analysis indicated: (δ, CDCl$_3$) 6.46 (s, 2H), 5.04 (s, 1H, OH), 2.66 (q, J=7 Hz, 2H), 2.34 (s, 3H) and 1.13 (t, J=7 Hz, 3H). Mass spectrum analysis indicated: (m/e) 262 (M+), 247 and 91.

(b) O-Methyl-3-ethyl-4-iodo-5-methylphenol; $^1$H NMR analysis indicated: (δ, CDCl$_3$) 6.45 (s, 2H), 3.60 (s, 3H), 2.67 (q, J=7 Hz, 2H), 2.35 (s, 3H) and 1.17 (t, J=7 Hz, 3H). Mass spectrum analysis indicated: (m/e) 276 (M+), 261, 134, 119 and 91.

(c) Methyl (Z)-α-acetamido-β-(2-ethyl-4-methoxy-6-methylphenyl)acrylate; $^1$H NMR analysis indicated: (δ, CDCl$_3$) 7.00 (s, 1H), 6.82 (s, 1H), 6.50 (s, 2H), 3.72 (s, 3H), 3.66 (s, 3H), 2.48 (q, J=7 Hz, 2H), 2.17 (s, 3H), 1.88 (s, 3H) and 1.14 (t, J=7 Hz, 3H). Mass spectrum analysis indicated: (m/e) 291 (M.), 232, 190 and 173.

(d) N-Acetyl-0-methyl-2-ethyl-6-methyl-(S)tyrosine methyl ester; This was obtained as a 97/3 mixture of S and R isomers, respectively, from the asymmetric hydrogenation step using the [Rh(COD)(R,R-DIPAMP)]BF$_4$ catalyst. $^1$H NMR analysis indicated: (δ, CDCl$_3$) 6.55 (br d, J=7 Hz, 1H, NH), 6.45 (s, 2H), 4.67 (q, J=7 Hz, 1H), 3.71 (s, 3H), 3.53 (s, 3H), 3.03 (AB of an ABX, 2H), 2.62 (q, J=7 Hz, 2H), 2.27 (s, 3H), 1.92 (s, 3H) and 1.17 (t, J=7 Hz, 3H).

(e) 2-Ethyl-6-methyl-(S)-tyrosine hydrobromide salt; $^1$H NMR analysis indicated: (δ, CD$_3$CN) 4.08 (m, 1H), 3.30 (d, J=7 Hz, 2H), 2.58 (q, J=7 Hz, 2H), 2.22 (s, 3H) and 1.12 (t, J=7 Hz, 3H).

(f) N-t-Butyloxycarbonyl-2-ethyl-6-methyl-(S)-tyrosine; mp 153-154° C., $^1$H NMR analysis indicated: (6, De-acetone) 6.54 (s, 1H), 6.51 (s, 1H), 6.08 (br d, J=7 Hz, 1H, NH), 4.39-4.30 (m, 1H), 3.17 (dd, J=6.8 and 14.7 Hz, 1H), 3.01 (dd, J=8.9 and 14.7 Hz, 1H), 2.68 (q, J=7 Hz, 2H), 2.31 (s, 3H), 1.37 (s, 9H) and 1.18 (t, J=7 Hz, 3H). Mass spectrum analysis indicated: (m/e) 346 (M+Na), 324 (M+H), 268, 224 and 149; Elemental Analysis was performed and calculated as follows: C$_{17}$H$_{25}$NO$_5$: C(63.15), H(7.73) and N(4.33), Found: C(62.25), H(7.63) and N(4.18). This material was shown to be a 99:1 ratio of S and R isomers, respectively.

EXAMPLE 7

N-Butyloxycarbonyl-2,6-dimethyl-(S)-phenylalanine This compound was prepared from 2,6-dimethyliodobenzene by the procedure used to prepare N-butyloxycarbonyl-2,6-dimethyl-(S)-tyrosine, in Example 1, except that the hydrolysis step was done using 12N hydrochloric acid. The physical characterization of the various intermediates is listed below.

(a) Methyl (Z)-α-acetamido-β-(2,6-dimethyl-phenyl)acrylate; mp 134°-135° C.; $^1$H NMR analysis indicated: (δ, CDCl$_3$) 7.21-7.05 (m, 4H), 6.63 (br s, 1H), 3.89 (s, 3H) and 2.24 (s, 6H). Mass spectrum analysis indicated: (m/e) 247 (M+), 205, 188, 146 (100%) and 43.

(b) N-Acetyl-2,6-dimethyl-(S)-phenylalanine methyl ester; This was obtained as a 97.5:2.5 mixture of S and R isomers, respectively, using the Rh(COD)(R,R-DIPAMP)]BF$_4$ catalyst. H NMR analysis indicated: (δ, CDCl$_3$) 7.07-6.96 (m, 3H), 6.03 (br d, J=7.5 Hz, 1H), 4.87-4.76 (m, 1H), 3.62 (s, 3H), 3.17-3.03 (m, 2H) and 2.34 (s, 6H). Mass spectrum analysis indicated: (m/e) 249 (M+), 119 (100%), 88 and 43.

(c) 2,6-Dimethyl-(S)-phenylalanine hydrochloride salt; $^1$H NMR analysis indicated: (δ, CD$_3$OD) 7.04 (s, 3H), 4.06 (t, J=8.0 Hz, 1H), 3.37 (dd, J=8.0 and 13.9 Hz, 1H), 3.16 (dd, J=8.0 and 13.9 Hz, 1H) and 2.35 (s, 6H). Mass spectrum analysis indicated (m/e), 194 (M+, 100%), 193, 178, 148, 131 and 119.

(d) N-t-Butyloxycarbonyl-2,6-dimethyl-(S)phenylalanine; mp 136-137° C.; $^1$H NMR analysis indicated: (δ, d$_6$-acetone) 6.98 (s, 3H), 6.20 (br d, J=8.7 Hz, 1H), 4.46 (dt, J=6.2 and 8.7 Hz, 1H), 3.26 (dd, J=6.2 and 13.9 Hz, 1H), 3.12 (dd, J=8.7 and 13.9 Hz, 1H), 2.38 (s, 6H) and 1.35 (s, 9H). Mass spectrum analysis indicated: (m/e) 294 (M+H), 238 (100%) and 194; Elemental Analysis was performed and calculated as follows: C$_{16}$H$_{23}$NO$_3$: C (65.51), H (7.89) and N (4.77), Found: C (65.71), H (7.97) and N (4.54); and [α]D$^{25}$=−15.6 (c =5.6 mg/ml, EtOH. This material was shown to be a 99:1 ratio of S and R isomers, respectively.

We claim

1. A process for the production of predominantly one enantiomorph of a 2,6-disubstituted phenyl amino acid of the structure:

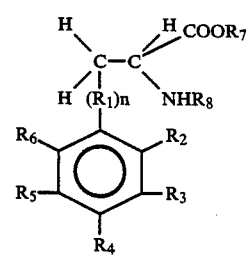

wherein $R_1$ is methylene or ethylene, n is 1 or 1, $R_2$ and $R_6$ are independently alkyl, aryl, chloro, fluoro, alkoxy, carboalkoxy or nitro and $R_3$, $R_4$ and $R_5$ are independently hydrogen, alkyl, aryl, chloro, fluoro, alkoxy, carboalkoxy or nitro, $R_7$ is an acid-protecting group and $R_8$ is an amine-protecting group, comprising:

(1) coupling a substituted phenyl compound of the structure:

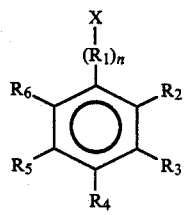

wherein X is bromo, iodo, or diazonium, with an acylamino acrylate of the structure:

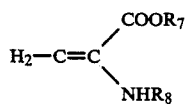

to form a substituted Z-3-(disubstituted phenyl) amino-protected acrylate of the structure:

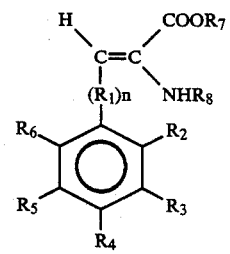

and (2) asymmetrically hydrogenating the acrylate obtained to form the desired enantiomorph of the 2,6-disubstituted phenyl amino acid.

2. The process of claim 1 wherein the substituted phenyl compound is selected from the group consisting of 2,6-dimethylphenyl iodide, 2,4,6-trimethylphenyl iodide, 4-methoxy-2-methyl-6-trifluoromethylphenyl iodide, 4-methyoxy-2,6-dimethylphenyl iodide, 4-benzyloxy-2,6-dimethylphenyl iodide and 4-acetoxy-2,6-diemthylphenyl iodide.

3. The process of claim 1 wherein $R_8$ is selected from the group consisting of acetyl, benzoyl, formyl, carbobenzoxy, 9-fluorenylmethyloxycarbonyl, 2-(4-biphenyl) propyl(2)oxycarbonyl, 2-phenyl-propyl(2)oxycarbonyl and t-butyloxycarbonyl and $R_7$ is selected from the group consisting of t-butyl, methyl, benzyl, beta-(trimethylsilylethyl) and trisubstituted silyl.

4. The process of claim 1 wherein the coupling is catalyzed by a catalyst selected from the group consisting of palladium, nickel or rhodium catalyst.

5. The process of claim 4 wherein the catalyst is selected from the group consisting of palladium diacetate, tetrakis(triphenylphosphine)palladium(0) and palladium dibenzylideneacetone.

6. The process of claim 4 wherein a trivalent phosphorous or arsenic ligand is used with the catalyst.

7. The process of claim 6 wherein the ligand is selected from the group consisting of tri-ortho-tolylphosphine, triphenylphosphine, tri-n-butyl phosphine, trimethylphosphine, triethylphosphine, diphenylmethyl phosphine, and triphenyl arsine.

8. The process of claim 1 wherein the asymmetric hydrogenation is catalyzed by a coordination complex of a metal selected from the group consisting of rhodium, iridium, ruthenium, osmium, palladium or platinum.

9. The process of claim 8 wherein the catalyst is a complex with a phosphine or arsine moiety of $AR_9R_{10}R_{11}$ wherein A is phosphorus or arsenic and $R_9$, $R_{10}$ and $R_{11}$ are each independently selected from the group consisting of alkyl, substituted alkyl, phenyl and substituted phenyl, and wherein at least one of the moieties $AR_9R_{10}R_{11}$ are optically active.

10. The process of claim 9 wherein the hyrogenation catalyst is a complex of the formula

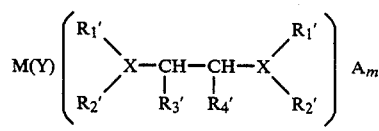

where M is a metal selected from a group consisting of Rh, Ir, Ru and Os, Y is a chelating diene or two monodentate olefins, $R_1$ and $R_2$ are aryl or substituted aryl groups, $R_3$ and $R_4$ are alkyl, H or aryl substitutents, X is phosphorous or arsenic, A is an anion selected from the group consisting of $PF_6^-$, $ClO_4^-$, $BF_4^-$, $CF_3SO_3^-$, $Cl^-$, and $Br^-$, and m is 1 or 2.

11. A process for the production of predominantly one enantiomorph of a 2,6-disubstituted phenyl amino acid of the structure:

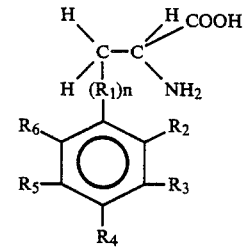

wherein $R_1$ is methylene or ethylene, n is 0 or 1, $R_2$ and $R_4$ are independently alkyl, aryl, chloro, fluoro, alkoxy, carboalkoxy or nitro and $R_3$, $R_4$ and $R_5$ are independently hydrogen, alkyl, aryl, chloro, fluoro, alkoxy, carboalkoxy or nitro, comprising (1) coupling a substituted phenyl compound of the structure:

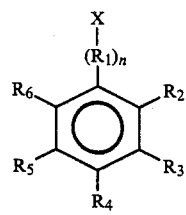

wherein X is bromo, iodo, or diazonium and n is 0 or 1, with an acylamino acrylate of the structure:

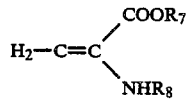

wherein $R_7$ is an acid-protecting group and $R_8$ is an aminoprotecting group, to form a substituted Z-3(disubstituted phenyl) amino-protected acrylate of the structure:

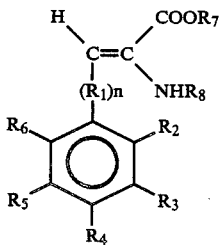

(2) asymmetrically hydrogenating the acrylate obtained to form the desired enantiomorph of the 2,6 disubstituted phenyl amino acid,
(3) deprotecting the protected 2,6 disubstituted phenyl amino acid.

12. The process of claim 11 wherein the protected amino acid is deprotected by strong acid treatment with an acid selected from the group consisting of hydrochloric acid and hydrobromic acid.

* * * * *

UNITED STATES PATENT AND TRADEMARK OFFICE
CERTIFICATE OF CORRECTION

PATENT NO. : 4,879,398

DATED : November 7, 1989

INVENTOR(S) : Daniel P. Getman et al

Page 1 of 2

It is certified that error appears in the above–identified patent and that said Letters Patent is hereby corrected as shown below:

Col. 2, line 11, delete "n is 0 or".

Col. 9, line 17, delete "whit" and substitute therefor —white—.

Col. 11, line 26, delete "$CDCl_z$" and substitute therefor —$CDCl_3$—.

Col. 11, line 61, delete "$NH_z$" and substitute therefor —$NH_2$—.

Col. 12, line 20, delete "(M)" and substitute therefor —$M^+$—.

Col. 13, line 47, delete "(M)" and substitute therefor —$M^+$—

Col. 13, line 60, delete "i" and substitute therefor —in—.

Col. 14, line 50, delete "(M)" and substitute therefor —$M^+$—

Col. 15, line 48, delete "(M.)" and substitute therefor —$M^+$—

Col. 17, line 1, delete "1", first occurrence, and substitute therefor —0—.

Col. 18, line 28, after the first "a" add —transition—.

Col. 18, line 30, delete "$R_1$ and $R_2$" and substitute therefor —$R'_1$ and $R'_2$—.

Col. 18, line 31, delete "$R_3$ and $R_4$" and substitute therefor —$R'_3$ and $R'_4$—.

UNITED STATES PATENT AND TRADEMARK OFFICE
CERTIFICATE OF CORRECTION

PATENT NO. : 4,879,398

DATED : November 7, 1989

INVENTOR(S) : Daniel P. Getman et al

It is certified that error appears in the above-indentified patent and that said Letters Patent is hereby corrected as shown below:

Col. 18, line 31, delete "$R_3$ and $R_4$" and substitute therefor —$R'_3$ and $R'_4$—.

Signed and Sealed this

Twenty-eighth Day of December, 1993

Attest:

BRUCE LEHMAN

Attesting Officer

Commissioner of Patents and Trademarks